US009427270B2

(12) United States Patent
Housman

(10) Patent No.: US 9,427,270 B2
(45) Date of Patent: Aug. 30, 2016

(54) REDUCED AREA THREAD PROFILE FOR AN OPEN ARCHITECTURE ANCHOR

(71) Applicant: Smith & Nephew, Inc., Andover, MA (US)

(72) Inventor: Mark Edwin Housman, North Attleborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 185 days.

(21) Appl. No.: 13/827,870

(22) Filed: Mar. 14, 2013

(65) Prior Publication Data
US 2014/0277192 A1    Sep. 18, 2014

(51) Int. Cl.
A61B 17/86    (2006.01)
A61B 17/04    (2006.01)
A61F 2/08     (2006.01)
A61B 17/88    (2006.01)

(52) U.S. Cl.
CPC ....... *A61B 17/8625* (2013.01); *A61B 17/0401* (2013.01); *A61B 17/869* (2013.01); *A61F 2/0811* (2013.01); *A61B 17/8875* (2013.01); *A61B 2017/0409* (2013.01); *A61B 2017/0414* (2013.01); *A61B 2017/0441* (2013.01); *A61B 2017/0445* (2013.01)

(58) Field of Classification Search
CPC .................. A61B 17/0401; A61B 2017/0441; A61B 2017/0443
USPC .................................. 403/229; 411/392, 438
See application file for complete search history.

(56) References Cited

U.S. PATENT DOCUMENTS

| 3,316,795 | A | * | 5/1967 | Tann | 411/17 |
| 4,961,740 | A | * | 10/1990 | Ray et al. | 606/247 |
| 5,055,104 | A | * | 10/1991 | Ray | 606/247 |
| 5,312,214 | A | * | 5/1994 | Morton | 411/17 |
| 5,464,427 | A | | 11/1995 | Curtis et al. | |
| 5,681,352 | A | | 10/1997 | Clancy et al. | |
| 6,146,073 | A | * | 11/2000 | Kobusch | 411/178 |
| 6,551,320 | B2 | * | 4/2003 | Lieberman | A61B 17/7022 606/263 |

(Continued)

FOREIGN PATENT DOCUMENTS

FR    2846867 A1    5/2004
WO    2010017631 A1    2/2010

OTHER PUBLICATIONS

International Search Report and Written Opinion dated Jun. 27, 2014 for PCT/US14/22562.

(Continued)

*Primary Examiner* — David Bates
(74) *Attorney, Agent, or Firm* — Burns & Levinson LLP; Joseph M. Maraia

(57) ABSTRACT

The disclosure provides examples of an open architecture anchor for securing soft tissue to bone, for example, to repair a torn rotor cuff. The anchor includes a helical screw thread having a base and two sidewalls that are non-linear. The non-linear sidewalls extend from opposing ends of the base and meet at a peak. The non-linear sidewalls are circumscribed within a triangle defined by the peak and ends of the base. Compared to the standard triangle profile, the helical screw thread profile has a smaller cross-sectional surface area and, consequently, removes less bone. The helical screw thread having the reduced cross-sectional area preserves bone stock and enhances the holding strength of the anchor in bone.

17 Claims, 3 Drawing Sheets

(56) References Cited

U.S. PATENT DOCUMENTS

| | | | |
|---|---|---|---|
| 7,189,251 B2* | 3/2007 | Kay | A61B 17/0401 411/395 |
| 7,935,138 B1* | 5/2011 | Richelsoph | 606/313 |
| 2002/0087161 A1* | 7/2002 | Randall et al. | 606/73 |
| 2003/0078585 A1* | 4/2003 | Johnson et al. | 606/72 |
| 2003/0181913 A1* | 9/2003 | Lieberman | 606/61 |
| 2004/0073216 A1* | 4/2004 | Lieberman | 606/61 |
| 2005/0143823 A1* | 6/2005 | Boyd et al. | 623/17.16 |
| 2005/0222681 A1* | 10/2005 | Richley et al. | 623/17.11 |
| 2006/0058797 A1* | 3/2006 | Mathieu et al. | 606/69 |
| 2006/0142769 A1 | 6/2006 | Collette | |
| 2007/0270839 A1* | 11/2007 | Jeon et al. | 606/61 |
| 2008/0004626 A1* | 1/2008 | Glazer et al. | 606/73 |
| 2008/0154314 A1* | 6/2008 | McDevitt | 606/304 |
| 2009/0076544 A1 | 3/2009 | Dimatteo et al. | |
| 2009/0118776 A1 | 5/2009 | Kelsch et al. | |
| 2009/0319043 A1* | 12/2009 | McDevitt et al. | 623/13.14 |
| 2010/0094352 A1* | 4/2010 | Iott et al. | 606/301 |
| 2011/0319933 A1 | 12/2011 | Tepic | |
| 2012/0101526 A1 | 4/2012 | Bennett | |
| 2012/0179163 A1* | 7/2012 | Housman et al. | 606/104 |
| 2013/0158599 A1* | 6/2013 | Hester | A61B 17/0401 606/232 |
| 2014/0277188 A1* | 9/2014 | Poulos | 606/304 |

OTHER PUBLICATIONS

International Preliminary Report for related PCT Application No. PCT/US2014/022562 dated Sep. 24, 2015.

* cited by examiner

REDUCED AREA THREAD PROFILE FOR AN OPEN ARCHITECTURE ANCHOR

BACKGROUND

Arthroscopic surgery is a minimally invasive surgical procedure in which an examination and sometimes treatment of damage of the interior of a joint is performed using an arthroscope, a type of endoscope that is inserted into the joint through a small incision. Arthroscopic procedures, such as repairing a torn rotor cuff, often require soft tissue to be reattached to bone. To achieve this, anchors (sometimes called "suture anchors") are placed in the bone and sutures attached to the anchor are passed through the tissue to securely retain the tissue in place.

SUMMARY

With the use of structurally weaker implant materials, such as bioabsorble composites, in open construct (architecture) anchors, the width of a thread profile base must be enlarged in order for threads to maintain structural integrity. Structural integrity is lost for open construct anchors when the thread separates from anchor rib(s) or the threads break. While providing the structural strength required, increasing thread cross sectional area reduces the amount of bone stock remaining after implant insertion. Preservation of bone stock and maintenance of thread height/depth with increased standard triangle thread profiles required by bioabsorable materials is therefore problematic.

The foregoing needs are addressed by an open construct anchor having a profile that is smaller than the standard triangle thread profile. This new thread profile has the same width (base) and height as the standard triangle thread profile but is circumscribed within the standard triangle thread profile. The cross-sectional area of the new thread profile is thus, smaller than the cross-sectional area of the standard triangle thread profile. Using a thread profile with a reduced cross-sectional area preserves bone stock and enhances anchor fixation.

Accordingly, in one aspect, the present disclosure relates to an anchor for securing soft tissue to bone, for example, to repair a torn rotor cuff. The anchor includes at least one open helical screw thread. The at least one open helical screw thread defines an internal volume communicating with a region exterior to the at least one open helical screw thread through a spacing between turns of the at least one open helical screw thread. The at least one open helical screw thread includes a base adjacent the internal volume. The base has a first end and second end. The at least one open helical screw thread further includes two non-linear side walls extending from the base to form a peak. The two non-linear side walls are each circumscribed within a triangle defined by the first end, second end, and peak. The anchor also includes at least one rib disposed within the internal volume, connected to at least two turns of the at least one open helical screw thread.

In another aspect, the present disclosure relates to a delivery device and anchor combination for securing soft tissue to bone, for example, to repair a torn rotor cuff. The delivery device of the combination includes a handle and shaft connected to the handle. The shaft includes distal end having at least one groove extending towards a proximal end of the shaft. The anchor of the combination includes at least one open helical screw thread. The at least one open helical screw thread defines an internal volume communicating with a region exterior to the at least one open helical screw thread through a spacing between turns of the at least one open helical screw thread. The at least one open helical screw thread includes a base adjacent the internal volume. The base has a first end and second end. The at least one open helical screw thread further includes two non-linear side walls extending from the base to form a peak. The two non-linear side walls are each circumscribed within a triangle defined by the first end, second end, and peak. The anchor also includes at least one rib disposed within the internal volume, connected to at least two turns of the at least one open helical screw thread. The anchor located on the distal end of the delivery device such that the at least one groove engages the at least one rib of the anchor.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The foregoing and other objects, features, and advantages will be apparent from the following more particular description of the embodiments as illustrated in the accompanying drawings in which like reference characters refer to the same parts throughout the different views. The drawings are not necessarily to scale, emphasis instead being placed upon illustrating the principles, characteristics, and features of the embodiments. In the drawings.

DETAILED DESCRIPTION

The following description of examples is in no way intended to limit the disclosure, its application, or uses.

Figure 1:
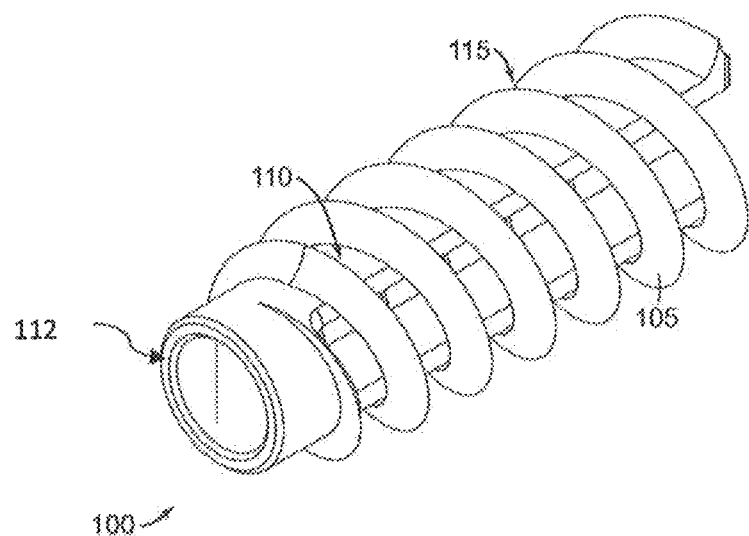
FIG. 1 is an isometric view of an example open architecture anchor.
Figure 2:
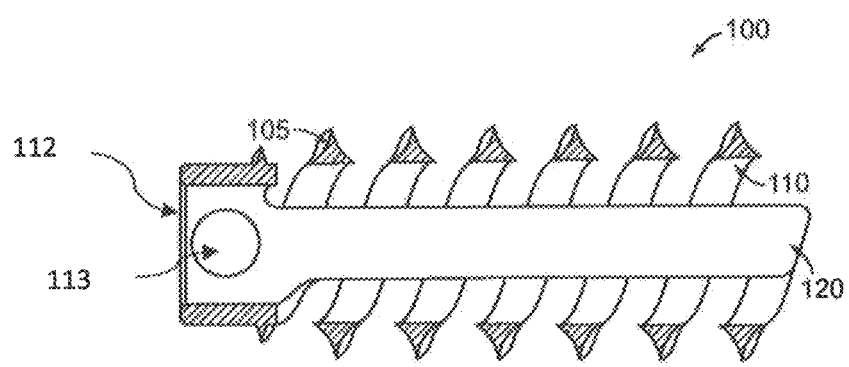
FIG. 2 is a cross-sectional view of the example open architecture anchor of FIG. 1.

FIGS. 1 and 2 show an example of an anchor 100 including at least one (open) helical screw thread 105, a cannulation 112 extending the length of the anchor 100 and defining an internal volume 110, and a through hole 113 located at the distal end of the anchor 100, configured for housing of a suture. The internal volume 110 communicates with a region exterior to the at least one open helical coil screw 105 through a spacing 115 between turns of the helical screw thread 105. After the anchor 100 is inserted to bone and the patient begins to heal, new hone grows into the internal volume 110 through the spacing 115. For faster and healthier healing "bony ingrowth" is highly desirable.

The anchor 100 further includes at least one rib 120 (two as shown) connected to at least two turns of the helical screw thread 105. Each respective rib 120 engages a corresponding groove of a delivery device. In use, the anchor 100 is located at a distal end of the delivery device such that each respective groove engages the respective rib 120 of the anchor 100. A surgeon inserts the anchor 100 into bone using the delivery device.

Some examples of the anchor 100 have two helical screw threads in a "dual lead" thread arrangement. Dual lead meaning two "ridges" are wrapped around the anchor 100. The anchor 100 may be constructed from, for example but not limited to, polymers (e.g., polyetheretherketone), bioabsorbable materials, metals (e.g., surgical steel, titanium), or any other suitable material.

Figure 3:
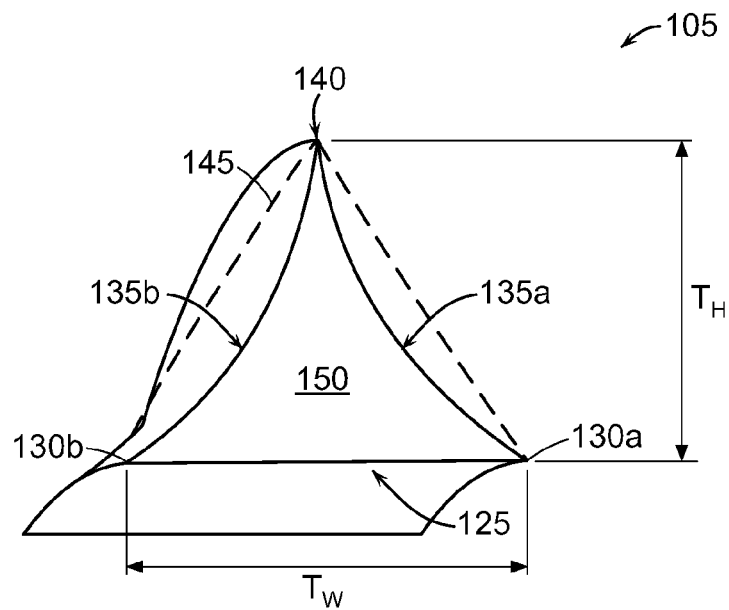
FIG. 3 is a cross-sectional view of an example of a helical screw thread.

FIG. 3 shows an example of the helical screw thread 105. The helical screw thread 105 includes a base 125 having a first end 130a and second end 130b. The helical screw thread 105 further includes two non-linear sidewalls 135a and 135b (generally 135) extending from the first and second ends 130a,b of the base 125 towards a peak 140. The first end 130a, second end 130b, and peak 140 form a base triangle 145 (shown in FIG. 3 as dashed lines). The non-linear sidewalls 135 are each circumscribed by the base triangle 145. One of the advantage s to foregoing geometry is that the anchor 100 can be smaller (e.g., in size and/or mass) then a screw with a standard triangular profile but have similar pullout strength. As shown, the non-linear sidewalls 135 have a concave profile; however, any profile circumscribed within the base triangle 145 is within the scope of this disclosure. Other example profiles of the helical screw thread 105 are described below.

The helical screw thread 105 may be further characterized as having a thread height ($T_H$) and thread width ($T_W$). An area 150 enclosed by the base 125 and non-linear sidewalls 135 is called the "cross-sectional area" The cross-sectional area 150 of the helical screw thread 105 is less than the cross-sectional area of a screw thread with a standard (conventional) triangle profile having the same thread width and height but having straight sidewalls instead. Advantageously, the anchor 100 removes less bone then a screw with a standard triangular profile resulting in less trauma to the patient. It may be convenient to describe the helical screw thread 105 and its examples as having a reduced cross-sectional area.

Figure 4:
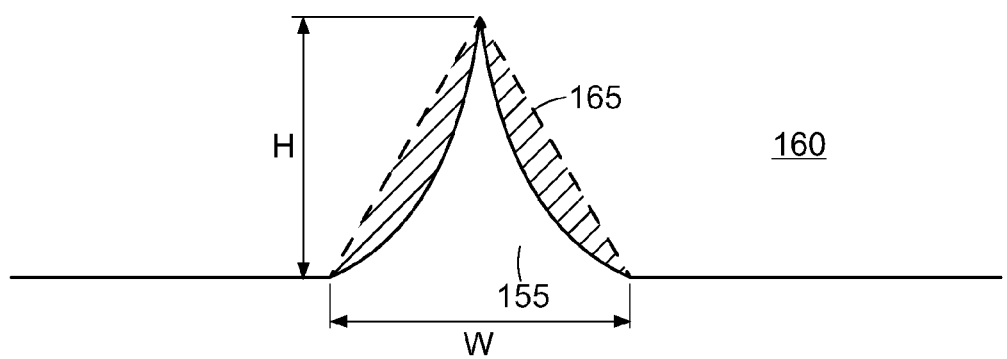
FIG. 4 is a cross-sectional view of a helical groove cut by of an example of a helical screw thread.

FIG. 4 shows part of a helical groove 155 cut into bone 160 by an example of the helical screw thread 105. The profile of the helical groove 155 is the inverse or reciprocal of the profile of the helical screw thread 105. In the example shown, the helical groove 155 has a convex profile cut by an example of the helical screw thread 105 having concave sidewalls (e.g., the helical screw thread 105 shown in FIG. 3.)

FIG. 4 also shows, as a series of dashed lines, the outline of a groove 165 cut by a screw thread with a standard triangle profile. The height (H) and width (W) of the helical groove 155 and the groove 165 are the same. The amount of the bone 160 removed in forming the helical groove 155, however, is less than the amount of bone removed in forming the groove 165. The hash marks represent bone not removed by the helical screw thread 105 that would be normally removed by the screw thread with the standard triangle profile. Thus, the reduced cross-sectional area 150 of examples of the helical screw thread 105 advantageously preserves bone stock.

The reduced cross-sectional area 150 by the helical screw thread 105 also maintains the same thread height as the conventional triangle profile. As such, the holding strength of the anchor 100 in the bone 160 is comparable to that of a typical anchor with a triangle-profiled thread. The anchor 100, however, achieves its strength by removing/displacing less bone stock than the typical anchor. Some examples of the helical screw thread 105 have an increased thread height to enhance pullout strength while minimizing the amount of bone stock displaced or removed.

As another advantage, the base 125 of the helical screw thread 105 can be enlarged without reducing the amount of bone preserved. Lengthening the base 125 (increasing the thread width) increases the connection strength between the helical screw thread 105 and rib 120 and, thereby, increases the structural strength of the anchor 100. In this example, the anchor 100 can withstand increased torsional loads, imparted by a delivery device, when inserting the anchor into the hard cortical (outer) layer of bone.

Yet another advantage, the anchor 100 and its examples reduce the amount of foreign material that is implanted into bone as contrasted with prior anchors with cross-sectional area larger than the reduced cross-sectional area 150. In turn, this promotes faster and healthier healing.

Returning to FIG. 3, the first and second non-linear sidewalls 135 have a concave profile. Additionally, the profile of the first non-linear sidewall 135a and profile of the second non-linear sidewall 135b are the same. It may be convenient to say that this example of the helical screw thread 105 has a symmetrical thread profile. Other profiles that can be circumscribed within the base triangle 145 are also within the scope of this disclosure.

Figure 5A:
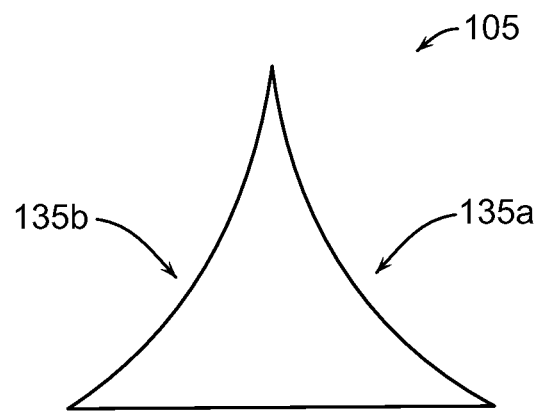
FIGS. 5A and 5B are cross-sectional views of example profiles of the helical screw thread.

FIG. 5A shows another example of the helical screw thread 105. The profile of the first non-linear sidewall 135a and the profile of the second non-linear sidewall 135b are different. It may be convenient to say that this example of the helical screw thread 105 has an asymmetrical thread profile.

Figure 5B:
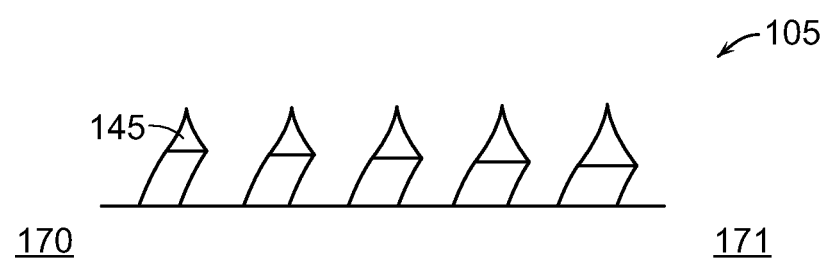

FIG. 5B shows yet another example of the helical screw thread 105 in which the cross sectional area 150 (or shape) varies along the length of the helical screw thread 105. As shown, the size of the cross sectional area 150 increases from a distal end 170 of the anchor 100 to a proximal end 171 of the anchor 100, i.e. the helical screw thread 105 has a non-constant cross-sectional area that varies along a helical trajectory.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described examples, but should be defined only in accordance with the following claims appended hereto and their equivalents.

What is claimed is:

1. A suture anchor for securing soft tissue to bone comprising:
   at least one open helical coil screw thread having a proximal end, a non-tapered distal end, and a longitudinal axis extending between the proximal and distal ends;
   a cannulation defining an internal volume extending the length of the suture anchor, the cannulation communicating with a region exterior to the at least one open helical coil screw thread through a spacing between turns of the at least one open helical coil screw thread, the at least one open helical coil screw thread comprising:
      a base adjacent the internal volume and having a first end and a second end;
      two non-linear side walls extending from the base to form a peak, wherein the two non-linear side walls are each circumscribed within a triangle defined by the first end, the second end, and the peak; and
   at least one rib disposed within the internal volume, connected to at least two turns of the at least one open helical screw thread coil;

wherein the distal end of the suture anchor comprises a non-threaded portion, the non-threaded portion having a through hole transverse to the longitudinal axis configured for housing a suture.

2. The suture anchor of claim 1 wherein the two non-linear side walls are concave in profile.

3. The suture anchor of claim 1 wherein one of the two non-linear side walls has a first profile and the other having a second profile same as the first profile.

4. The suture anchor of claim 1 wherein one of the two non-linear side walls has a first profile and the other having a second profile different than the first profile.

5. The suture anchor of claim 1 wherein the base and two non-linear side walls define a cross sectional shape that varies along the length of the least one open helical coil screw thread.

6. The suture anchor of claim 1 wherein the at least one open helical coil is a dual lead helical coil.

7. The suture anchor of claim 1, wherein the suture anchor comprises one of a polymer, a bioabsorbable material and a metal.

8. The suture anchor of claim 1, wherein the two non-linear sidewalls extend from the peak to the base adjacent the internal volume.

9. A delivery device and suture anchor combination, the combination comprising:
 a delivery device comprising a handle and shaft connected to the handle, the shaft including a distal end having at least one groove extending towards a proximal end of the shaft; and
 a suture anchor for securing soft tissue to bone comprising:
  at least one open helical coil screw thread having a proximal end, a non-tapered distal end, and a longitudinal axis extending between the proximal and distal ends;
  a cannulation defining an internal volume extending the length of the suture anchor, the cannulation communicating with a region exterior to the at least one open helical coil screw thread through a spacing between turns of the at least one open helical coil screw thread, the at least one open helical coil screw thread comprising:
   a base adjacent the internal volume and having a first end and a second end, and two non-linear side walls extending from the base to form a peak, wherein the two non-linear side walls are each circumscribed within a triangle defined by the first end, the second end, and the peak, and
   at least one rib disposed within the internal volume, connected to at least two turns of the at least one open helical screw thread coil,
  wherein the distal end of the suture anchor comprises a non-threaded portion, the non-threaded portion having a through hole transverse to the longitudinal axis configured for housing a suture; and
 wherein the suture anchor is located on the distal end of the delivery device such that the at least one groove engages the at least one rib of the suture anchor.

10. The delivery device and suture anchor combination of claim 9, wherein the suture anchor comprises one of a polymer, a bioabsorbable material and a metal.

11. The delivery device and suture anchor combination of claim 9, wherein the two non-linear sidewalls extend from the peak to the base adjacent the internal volume.

12. A suture anchor for securing soft tissue to bone comprising:
 at least one open helical coil screw thread having a proximal end, a distal end, and a longitudinal axis extending between the proximal and distal ends;
 a cannulation defining an internal volume extending the length of the suture anchor, the cannulation communicating with a region exterior to the at least one open helical coil screw thread through a spacing between turns of the at least one open helical coil screw thread, the at least one open helical coil screw thread comprising:
  a base adjacent the internal volume and having a first end and a second end;
  two non-linear side walls extending from the base to form a peak, one of the two non-linear side walls having a first profile and the other having a second profile different than the first profile, the two non-linear side walls each being circumscribed within a triangle defined by the first end, the second end, and the peak; and
  at least one rib disposed within the internal volume, connected to at least two turns of the at least one open helical screw thread coil;
 wherein the first profile and the second profile are asymmetrical to one another.

13. The suture anchor of claim 12, wherein the two non-linear side walls are concave in profile.

14. The suture anchor of claim 12, wherein the base and two non-linear side walls define a cross sectional shape that varies along the length of the least one open helical coil screw thread.

15. The suture anchor of claim 12, wherein the at least one open helical coil is a dual lead helical coil.

16. The suture anchor of claim 12, wherein the suture anchor comprises one of a polymer, a bioabsorbable material and a metal.

17. The suture anchor of claim 12, wherein the two non-linear sidewalls extend from the peak to the base adjacent the internal volume.

* * * * *